United States Patent
Chen et al.

(10) Patent No.: US 10,155,247 B2
(45) Date of Patent: Dec. 18, 2018

(54) MULTIPLE SCAFFOLD DESIGN AND COATING THEREOF

(71) Applicant: Abbott Cardiovascular Systems Inc., Santa Clara, CA (US)

(72) Inventors: Yung-Ming Chen, San Jose, CA (US); Henjen Ho, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 408 days.

(21) Appl. No.: 15/130,621

(22) Filed: Apr. 15, 2016

(65) Prior Publication Data
US 2016/0228912 A1 Aug. 11, 2016

Related U.S. Application Data

(62) Division of application No. 13/195,729, filed on Aug. 1, 2011.

(51) Int. Cl.
| | |
|---|---|
| A61F 2/82 | (2013.01) |
| B05D 1/02 | (2006.01) |
| B05B 13/04 | (2006.01) |
| A61L 31/16 | (2006.01) |
| A61L 31/08 | (2006.01) |

(Continued)

(52) U.S. Cl.
CPC ............... *B05D 1/02* (2013.01); *A61F 2/82* (2013.01); *A61L 31/08* (2013.01); *A61L 31/16* (2013.01); *B05B 12/18* (2018.02); *B05B 13/0442* (2013.01); *A61F 2/915* (2013.01); *A61F 2002/826* (2013.01); *A61F 2002/828* (2013.01); *A61F 2210/0004* (2013.01); *A61F 2250/0067* (2013.01); *A61F 2250/0071* (2013.01); *A61L 2420/02* (2013.01)

(58) Field of Classification Search
USPC ........................................................ 427/2.24
See application file for complete search history.

(56) References Cited

U.S. PATENT DOCUMENTS

| | | | | |
|---|---|---|---|---|
| 5,755,781 A | * | 5/1998 | Jayaraman | A61F 2/91 623/1.16 |
| 5,817,152 A | * | 10/1998 | Birdsall | A61F 2/90 623/1.16 |

(Continued)

FOREIGN PATENT DOCUMENTS

| | | |
|---|---|---|
| JP | 2002/541909 | 12/2002 |
| JP | 2005/519672 | 7/2005 |
| JP | 2010/507458 | 3/2010 |

OTHER PUBLICATIONS

Japanese Office Action dated May 31, 2016 for Japanese Patent Application No. P2014-524014, 4 pp.

(Continued)

*Primary Examiner* — Cachet I Sellman
(74) *Attorney, Agent, or Firm* — Squire Patton Boggs (US) LLP (57) ABSTRACT

A multiple stent structure including a plurality of stent bodies arranged end to end in which adjacent stent bodies of the structure are connected by a severable connecting portion disposed between the adjacent stent bodies is disclosed. A method of coating a plurality of stents including depositing a coating on the multiple stent structure and severing the severable connecting portions to disconnect the plurality of stent bodies is disclosed.

6 Claims, 9 Drawing Sheets

(51) Int. Cl.
   *B05B 12/18* (2018.01)
   *A61F 2/915* (2013.01)

(56) References Cited

U.S. PATENT DOCUMENTS

| | | | | |
|---|---|---|---|---|
| 5,893,887 | A * | 4/1999 | Jayaraman | A61F 2/91 623/1.15 |
| 6,258,117 | B1 * | 7/2001 | Camrud | A61F 2/82 623/1.16 |
| 6,344,055 | B1 * | 2/2002 | Shukov | A61F 2/91 29/896.6 |
| 6,572,647 | B1 * | 6/2003 | Supper | A61F 2/91 623/1.15 |
| 7,122,049 | B2 * | 10/2006 | Banas | A61F 2/91 623/1.15 |
| 7,137,993 | B2 * | 11/2006 | Acosta | A61F 2/915 623/1.11 |
| 2004/0167616 | A1 | 8/2004 | Camrud et al. | |
| 2006/0173529 | A1 * | 8/2006 | Blank | A61F 2/91 623/1.16 |
| 2007/0003688 | A1 * | 1/2007 | Chen | A61L 31/082 427/2.24 |
| 2007/0135897 | A1 * | 6/2007 | Chen | B05B 13/0235 623/1.16 |
| 2007/0213810 | A1 * | 9/2007 | Newhauser | A61F 2/91 623/1.16 |
| 2009/0061072 | A1 * | 3/2009 | Isch | A61F 2/88 427/2.25 |
| 2010/0010622 | A1 * | 1/2010 | Lowe | A61F 2/91 623/1.16 |
| 2010/0042202 | A1 * | 2/2010 | Ramzipoor | A61F 2/91 623/1.15 |
| 2016/0128851 | A1 | 5/2016 | Sheldon et al. | |

OTHER PUBLICATIONS

Translation of Japanese Office Action dispatched May 31, 2016 for Japanese Patent Application No. P2014-524014, 3 pp.

\* cited by examiner

MULTIPLE SCAFFOLD DESIGN AND COATING THEREOF

This application is a division of application Ser. No. 13/195,729 filed Aug. 1, 2011, which is incorporated by reference herein.

BACKGROUND

Stents act as scaffoldings, functioning to physically hold open and, if desired, to expand the wall of the passageway of a target vessel. Stents are often used in the treatment of atherosclerotic stenosis and/or restenosis in blood vessels. "Stenosis" refers to a narrowing or constriction of the diameter of a bodily passage or orifice. Typically, stents are capable of being compressed, so that they can be inserted through small cavities via catheters, and then expanded to a larger diameter once they reach their target vessel. Mechanical intervention via stents has reduced the rate of restenosis; restenosis, however, is still a significant clinical problem. "Restenosis" refers to the reoccurrence of stenosis in a blood vessel or heart valve after it has been treated (as by balloon angioplasty or valvuloplasty) with apparent success. Accordingly, stents have been modified to perform not only as a mechanical scaffolding, but also to provide biological therapy.

Biological therapy can be achieved by medicating a stent, typically referred to as a drug delivery stent. Drug delivery stents provide for the local administration of a therapeutic substance at the diseased site. In contrast, systemic administration of a therapeutic substance may cause adverse or toxic side effects for the patient because large doses are needed in order for the therapeutic substance to have an efficacious effect at the diseased site. Thus, local delivery is a preferred method of treatment in that smaller total levels of medication are administered in comparison to systemic dosages, but are concentrated at a specific site. Local delivery therefore produces fewer side effects and achieves more favorable results.

Stents may be made of biostable materials that remain at an implant site permanently. However, the clinical need for a stent at an implant site may be temporary. Once treatment is complete, which may include structural tissue support and/or drug delivery, it may be desirable for the stent to be removed or disappear from the treatment location. One way of having a stent disappear may be by fabricating a stent in whole or in part from materials that erode or disintegrate through exposure to conditions within the body. Stents fabricated from bioresorbable, biodegradable, bioabsorbable, and/or bioerodable materials such as bioresorbable polymers can be designed to completely erode only after the clinical need for them has ended.

A typical method for medicating an implantable device includes, for example, applying a composition containing a polymer, a solvent, and a therapeutic substance to the implantable device using conventional techniques, such as spray-coating or dip-coating. The method further includes removing the solvent, leaving on the implantable device surface a coating of the polymer with the therapeutic substance impregnated in the polymer.

In a typical spray-coating method, a stent is mounted on a mandrel of a spray-coating device. Generally, the stent will rest on, or contact components of, a mandrel (or the mandrel itself) which supports the stent and allows it to rotate during a spray-coating process. The contact between the portions of the mandrel and stent, however, inevitably cause coating defects. These defects can include cob-webbing, tearing, bridging, clumping and/or lack of coating on portions of the stent. The embodiments of the present invention are intended to address coating defect issues caused by conventional mandrel designs.

Another issue with conventional stent coating operations is one of efficiency and cost. Stent coating is typically performed one stent or scaffold at a time. For each stent coated, the coating equipment must be set up. In addition, each stent or scaffold must be loaded prior to coating and unloaded after coating. Thus, machine utilization is limited by coating only one stent for machine set-up, loading, and unloading processes.

SUMMARY

Various embodiments of the present invention include a medical device comprising: a structure comprising a plurality of stent bodies arranged end to end, wherein adjacent stent bodies of the structure are connected by a severable connecting portion disposed between the adjacent stent bodies, wherein at least one of the stent bodies at an end of the structure comprises a severable end portion at the end of the structure.

Further embodiments of the present invention include a method of coating a plurality of stents comprising: providing a structure comprising a plurality of stent bodies arranged end to end, wherein adjacent stent bodies along the structure are connected by a severable connecting portion disposed between the adjacent stent bodies; and depositing a coating on the plurality of stent bodies; and severing the severable connecting portions to disconnect the plurality of stent bodies.

DETAILED DESCRIPTION

The implantable medical device used in conjunction with the present invention may be any implantable medical device, examples of which include self-expandable stents, balloon-expandable stents, micro-depot or micro-channel stents, stent-grafts and grafts. Examples of stents include neurological, coronary, peripheral and urological stents. In some embodiments, the underlying structure of the implantable medical device can be virtually any design.

Figure 1:
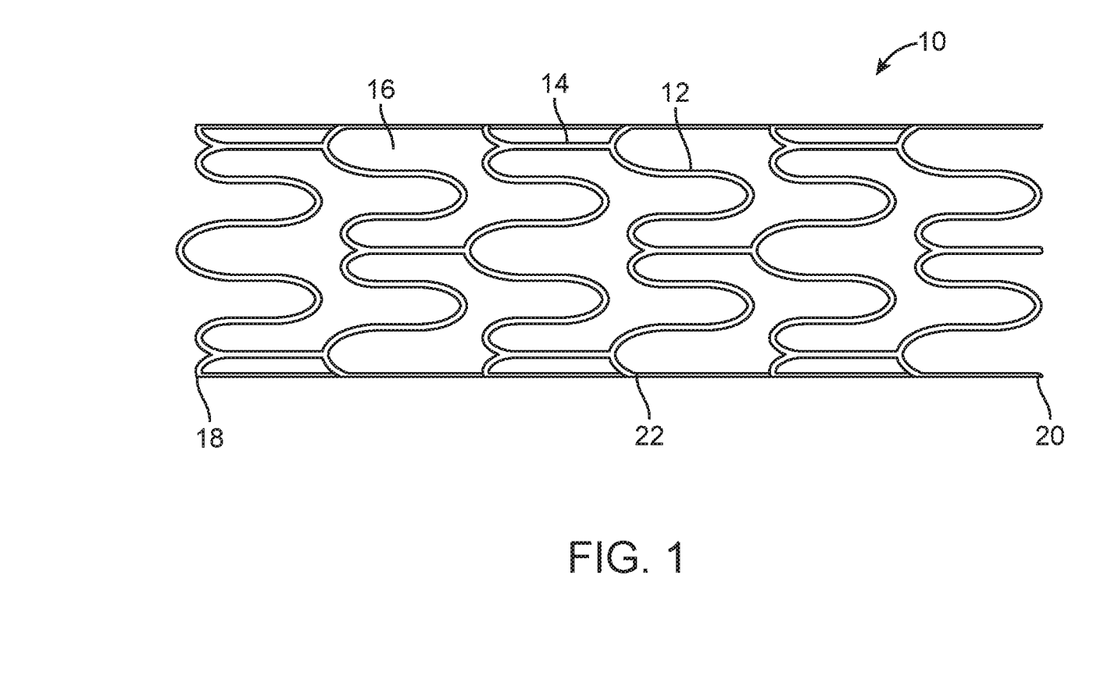
FIG. 1 illustrates an exemplary stent.

FIG. 1 illustrates a stent 10, which in various embodiments may be metallic or polymeric. In either form, the stent 10 can include a plurality of struts 12 linked by connecting elements 14, with the struts 12 and connecting elements 14 surrounding or partially surrounding interstitial spaces 16. The plurality of struts 12 can be configured in an annular fashion in discrete "rows" such that they form a series of "rings" throughout the body of the stent 10. Thus, the stent 10 can include a proximal ring 18, a distal ring 20 and at least one central ring 22.

A stent such as stent 10 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device of the present invention can be made partially or completely from a biodegradable, bioresorbable, bioabsorbable, or biostable polymer. A polymer for use in fabricating an implantable medical device can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

A stent made from a bioresorbable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

A therapeutic coating may be formed over a stent by applying a composition containing a polymer, a solvent, and a therapeutic substance to the stent using techniques, such as spray-coating or dip-coating. The solvent is then removed leaving a coating on the stent surface including the polymer with the therapeutic substance impregnated in the polymer.

Figure 2:
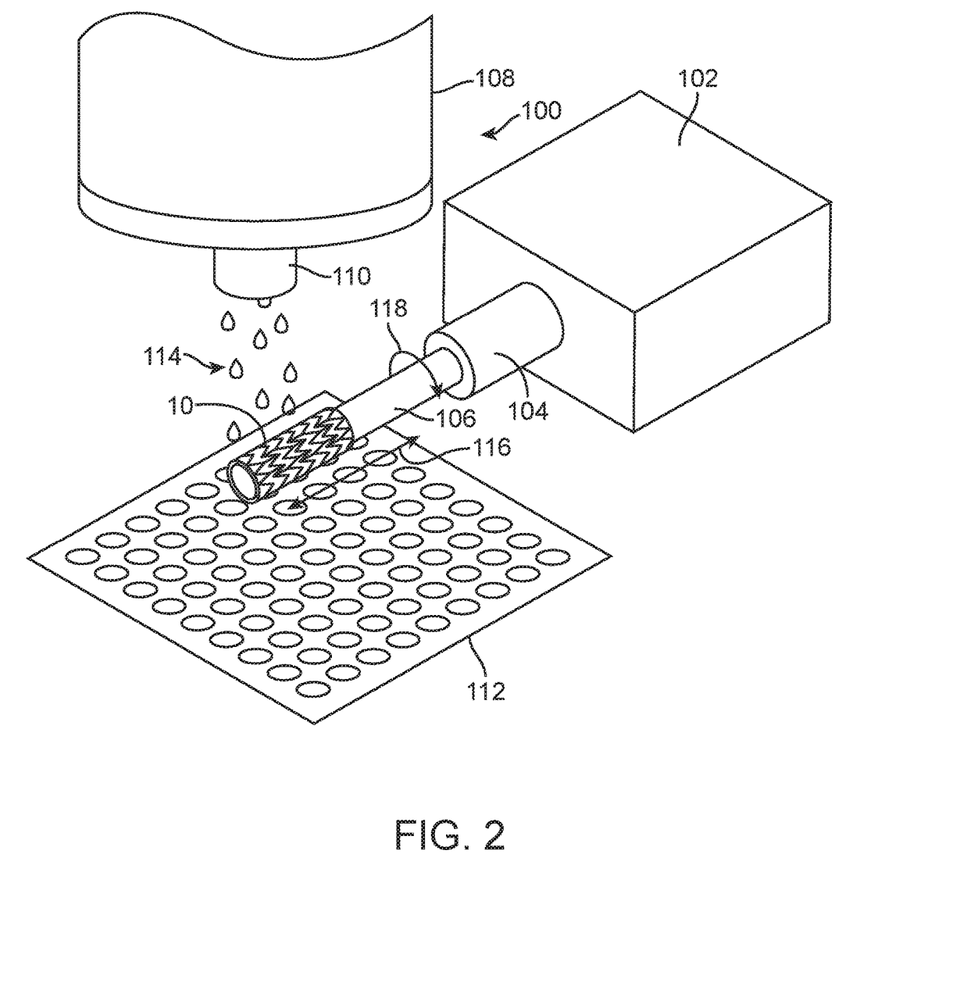
FIG. 2 illustrates a method of coating a stent with a spray-coating device.

FIG. 2 illustrates a prior art spray-coating device 100 and process for coating single stent. The spray-coating device 100 can include the following elements: a stent movement and rotating device 102, a support member 104 and a stent holding device 106 for rotation and movement of the stent 10 before, during and/or after the coating process; a nozzle 108 with an air shroud device 110 for spray-coating the stent 10; and an exhaust system 112 to remove excess spray from the target area on the stent 10. In some applications, the stent 10 can be mounted onto the stent holding device 106 forming an assembly thereof. The assembly can then be mounted into a socket of the support member 104 for coating with composition 114 from the air shroud 110 of the nozzle 108. In some applications, the stent movement and rotating device 102 can move the assembly in a linear direction (arrow 116) to achieve a targeted or uniform coating. In some applications, the support member 104 can rotate the assembly (arrow 118) to achieve a targeted or uniform coating. In some applications, a combination of linear and rotational movements can be used to coat the stent 10. The exhaust system 112 can function to remove excess composition during the spray-coating process.

In the spray-coating method described previously, there are contact areas between the stent 10 and the stent holding device 106. Depending on the stent and its holding device, contact areas are the source of the coating defects, in the form of cob-webbing, tearing, bridging, clumping and/or lack of coating on portions of the stent.

Figure 3A:
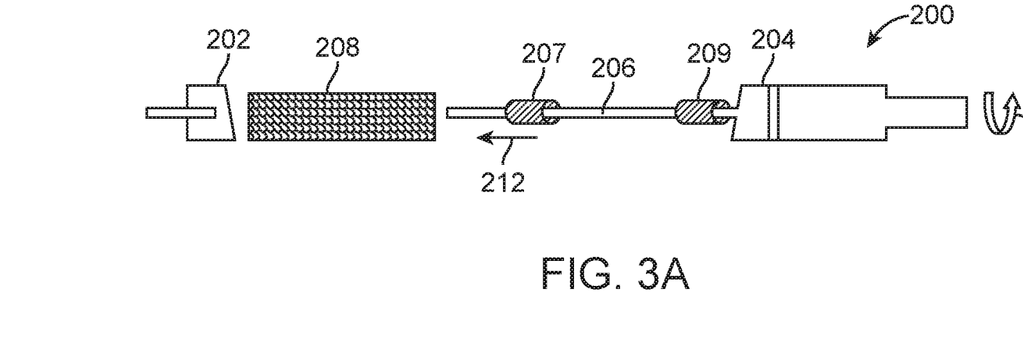
FIGS. 3A-B illustrates an alternative manner of supporting a stent during the coating process.
Figure 3B:
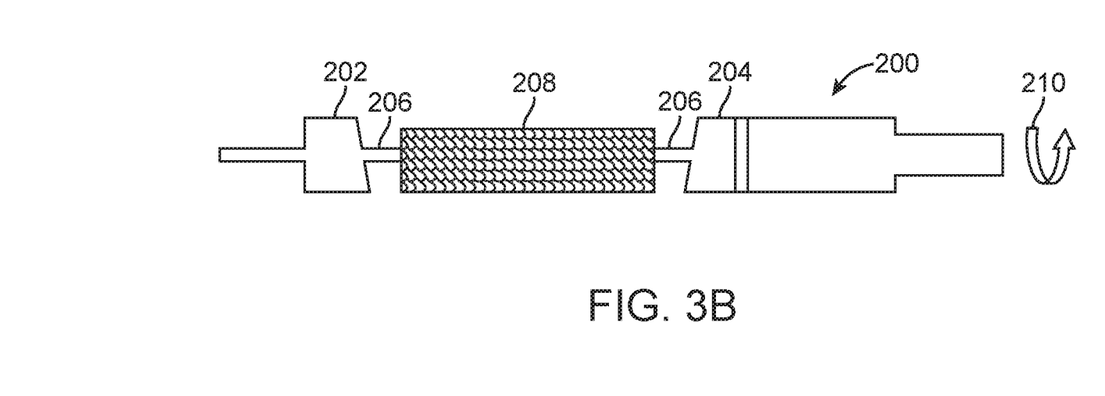

FIGS. 3A-B illustrates an assembly used in supporting a stent during the coating process. FIG. 3A depicts a core mandrel assembly 200 which contains a core wire 206 slanted collets 202 and 204 and mini coils 207 and 209. FIG. 3B is to show placement of a stent (arrow 212) and the final assembly with a stent 208. Coils 207 and 209 are used to provide minimal contact surface area to loosely support the stent 208 during the coating process. Mandrel assembly 200 rotates 210 during deposition of a coating composition on stent 208, but the stent is not rotating in one to one ratio compared to the mandrel assembly. Coils 207 and 209 have diameters and lengths significantly smaller than stent 208. Nevertheless, the contact of coils 207 and 209 can create coating defects in the stent's 208 inner surface, thus it leads to suboptimal coating quality.

Embodiments of the present invention solve both of the problems of the conventional coating methods by eliminating the contact defects and allowing coating of more than one stent during a coating process. The embodiments of the present invention include coating a multiple stent structure, which including a plurality of stent bodies arranged end to end in which adjacent stent bodies are connected by a severable support element disposed between the adjacent stent bodies. "End-to-end" is defined generally as with the end of one object in arranged lengthwise, such as along a cylindrical axis in the case of tubular objects, with the end of another object. "Adjacent stent bodies" refer to stent bodies in an end to end arrangement in the structure that are connected by a connecting portion and which have no intervening stent bodies between them. In further embodiments, the ends of stent bodies at one or both ends of the structure may also include severable portions or support elements.

In certain embodiments, the multiple stent structure is disposed over a stent support system. A coating is deposited on the multiple stent structure that is disposed over the stent support system. As described below, the multiple stent structure can include one or more of the severable portions or support elements that can engage the stent support system to allow deposition of coating material on the structure FIG. 7A-B and FIG. 8A-B. After the coating is formed over the structure and after an optional drying step, the severable portions are severed or removed to disconnect the plurality of stent bodies from one another to provide a plurality of disconnected coated stent bodies.

In some embodiments, a finished coating can be formed directly over the multiple stent structure composed of the plurality of stent bodies without unloading the stent structure from the support system. Therefore, the embodiments described allow coating multiple stent bodies without loading and unloading the stent bodies for each stent body. The plurality of stent bodies are coated in one coating operation. A coating operation refers to forming a coating over the stent structure which involves loading and unloading the stent structure on a support system. A stent body refers to a longitudinal section of a repeating pattern of struts, as described above, that is intended to be implanted into a patient and that does not include the severable support elements or the other stent bodies.

Figure 4A:
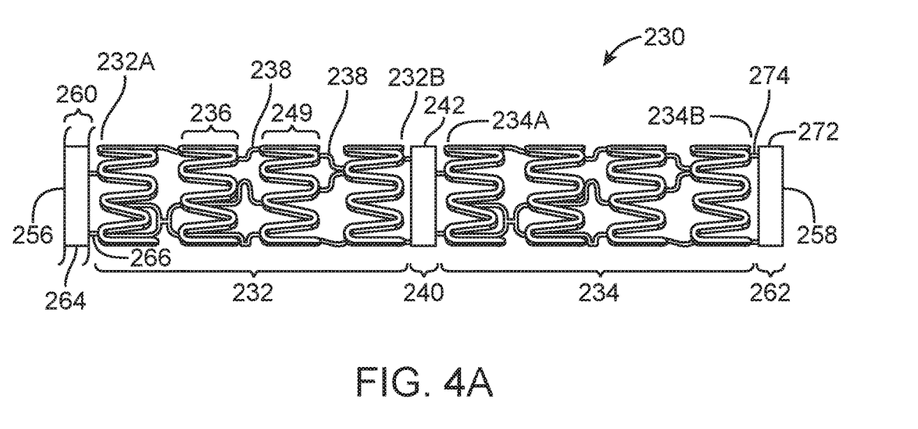
FIG. 4A depicts an exemplary multiple stent structure composed of two stent bodies connected by a severable portion.

FIG. 4A depicts an exemplary multiple stent structure 230 composed of two stent bodies 232 and 234 connected by a severable portion or support element 240. Structure 230 includes a stent body 232 and a stent body 234. Stent body 232 has a proximal end 232A and a distal end 232B and stent body 234 has a proximal end 234A and a distal end 234B. Stent bodies 232 and 234 each are scaffolds and each is made up of a pattern composed of interconnected structural elements. Specifically, stent bodies 232 and 234 include undulated cylindrical rings 236 and 249 connected by linking elements 238.

Figure 4B:
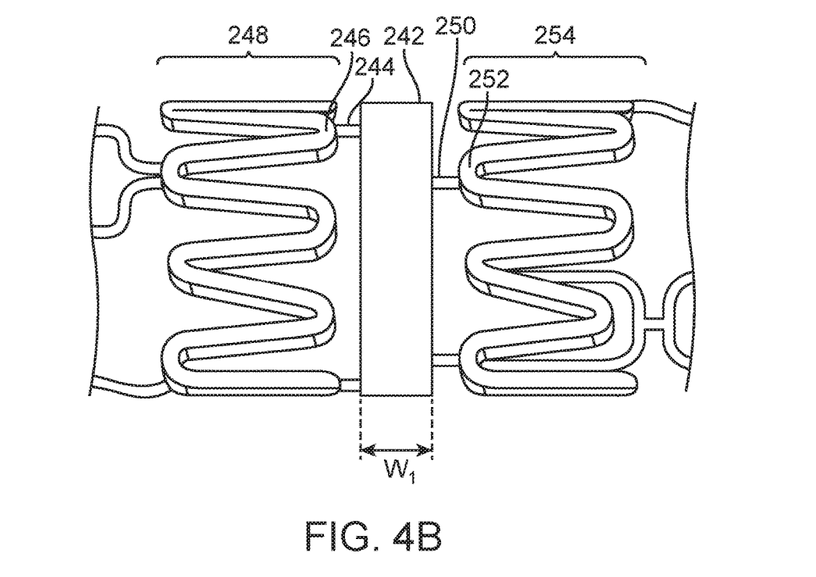
FIG. 4B depicts a close-up view of the severable portion of FIG. 4A.

FIG. 4B depicts a close-up view of severable portion 240, the severable portion 240 of multiple stent structure 230 includes a connecting band, ring, or tube 242 (terms which are used interchangeably unless otherwise used specifically). Severable portion 240 can alternatively include a tab. Tube 242 has a width W1.

Severable portion 240 also includes at least one "gate", flange or bar 244 (terms which are used interchangeably unless otherwise used specifically). Gate 244 connects tube 242 to distal end 232B of stent 232, specifically, to crest 246 of distal ring 248 of stent 232. Gate 250 connects tube 242 to proximal end 234A of stent 234, specifically, to crest 252 of proximal ring 254 of stent 234.

Figure 4C:
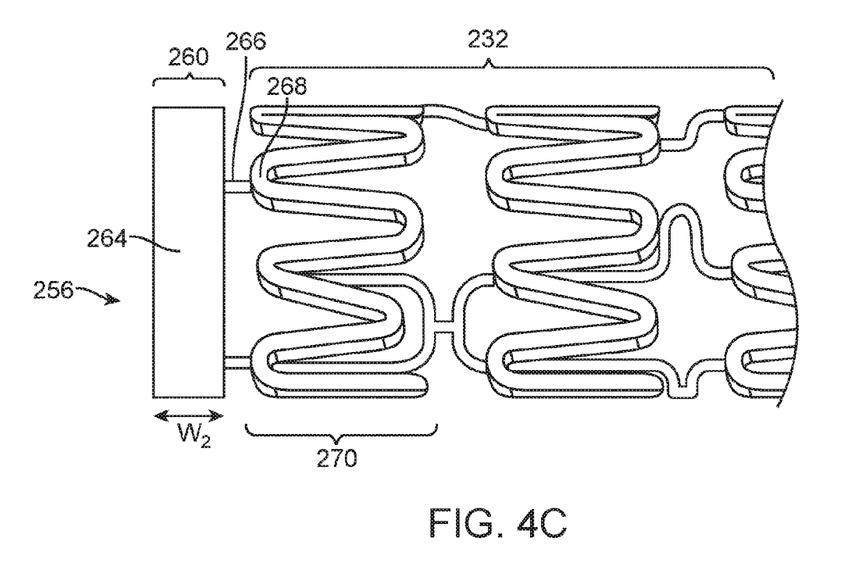
FIG. 4C depicts a close-up view of the proximal end of a multiple stent structure.

As indicated above, the ends of stent bodies at one or both ends of the multiple stent structure may also include severable support portions or elements. Referring to FIG. 4A, a proximal end 256 and a distal end 258 of multiple stent structure 230 include severable portions 260 and 262, respectively. FIG. 4C depicts a close-up view of proximal end 256 of multiple stent structure 230. Severable portion 260 includes an end tube 264 and at least one gate 266 that connects tube 264 to proximal end 232A of stent 232, specifically, to crest 268 of proximal ring 270 of stent 232. In FIG. 4A, severable portion 262 likewise includes end tube 272 and gate 274 connects tube 272 to distal end 234B of stent 234. Tubes 264 and 272 have a width W2.

Figure 5A:
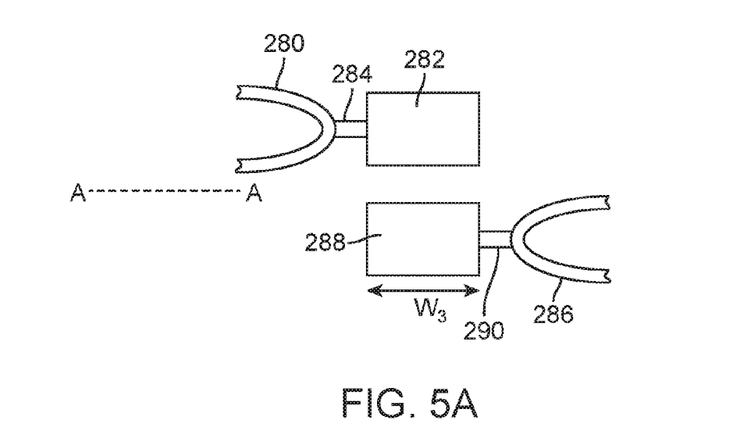
FIG. 5A depicts a strut that is a portion of a stent that is connected to a tab by a gate.

As an alternative to a tube or band for at the ends of the multiple stent structure and for connecting adjacent stent bodies, the severable portion may have at least one tab. FIG. 5A depicts a strut 280 and strut 286 that are a portions of adjacent stents in a multiple stent structure. Struts 280 and 286 are at two different circumferential positions of the multiple stent structure. Line A-A corresponds to the cylindrical axis of the multiple stent structure. Strut 280 is connected to a tab 282 by a gate 284. Strut 286 of the adjacent stent is connected to a tab 288 by a gate 290. The tabs have a width W3.

Figure 5B:
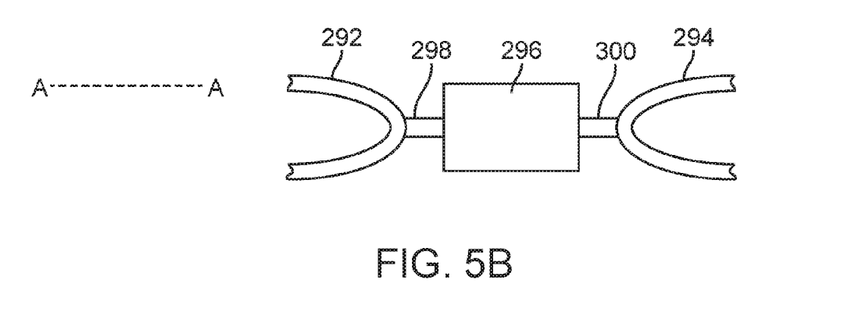
FIG. 5B depicts an alternative embodiment of stent bodies connected to a tab by gates.

FIG. 5B depicts an alternative embodiment in which the adjacent stent pattern is configured so that the crests of the adjacent struts 292 and 294 are at the same or slightly different circumferential position. Strut 292 is connected to tab 296 by gate 298 and strut 294 is connected to the same tab 296 by gate 300.

Figure 6:
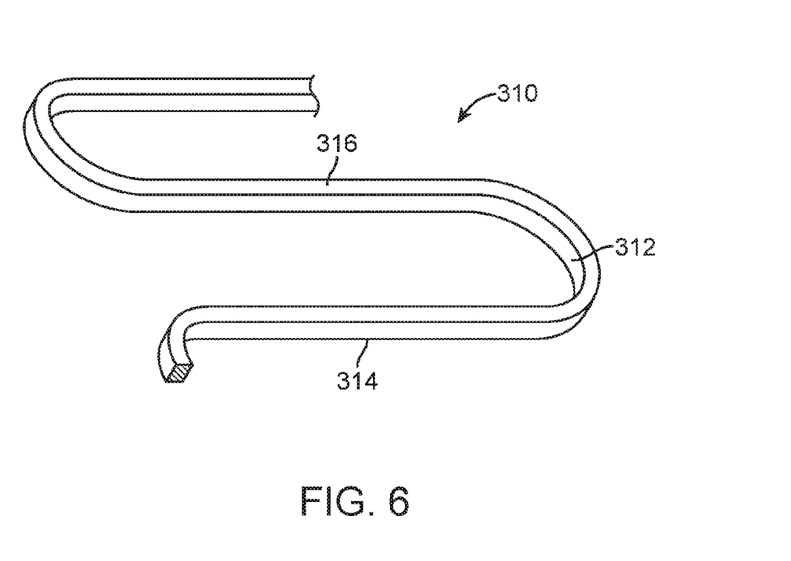
FIG. 6 depicts a portion of a stent showing a side wall, an inner surface, and an outer surface of a strut.

FIG. 6 depicts a portion 310 of a stent. A gate may be attached to a strut at a side wall 312, an inner surface 314, an outer surface 316 or any combination thereof of a stent.

In some embodiments, the stent bodies and one or more of the connecting tubes or tabs between adjacent stent bodies and end tubes at the proximal and distal ends of the structure can be monolithic. That is, when the stent pattern is originally cut or etched from a flat sheet or from a tube, the tubes or tabs of the pattern remain attached to the stent pattern by the at least one gate. Stent patterns can be formed by a variety of methods, including but not limited to, laser cutting and etching, such as chemical etching. Other stent pattern formation techniques may be utilized and are known by those skilled in the art.

In some embodiments, the end tubes or connecting tubes may be attached to the stent by a secondary process, such as, for example, by biocompatible glue or solder. In the process in which the stent pattern is cut into a flat sheet (as opposed to directly on a tube), the attaching may be done either after the cutting or after the cut pattern is rolled into a tube forming a stent thereof. In some embodiments, the severable portion can include, for example, a tab or tube attached to some portion of a stent body that is part of a multiple stent structure. Thus, FIG. 4A illustrates an embodiment in which a tube is attached to the sidewall (not shown in this figure) of a ring adjacent to the tube by a gate. In another alternative embodiment, the tube or tab is attached to at least one ring that is not adjacent to the tab or ring by an attachment, for example attaching tube 242 to a ring 249 in FIG. 4A. In any embodiment, the tubes or tabs can be attached monolithically or by secondary processes as explained above. Therefore, the at least one gate can be made from the same material as the stent body or made of different material. In some embodiments, the material for a gate, a tube, and a tab can be any of the polymeric and/or metallic materials disclosed below. For example, the gate can be made of the polymers from which the stent is made and/or coated.

The connecting and end portion(s) of the multiple stent structure, which may be at least one end tube or at least one tab, may function as the connecting support of the multiple stent structure to the spray-coating device (such as those illustrated in FIG. 2) before, during or after the spray-coating process and optionally a drying stage. The connecting portions are severable via the at least one gate on both sides of the connecting portions. For example, gates 244 that connect tube 242 to stent body 232 and gates 250 that connect tube 242 to stent body 234 in FIG. 4A are severed. Additionally, the end portions are severable via the at least one gate connecting the end portions to the proximal and distal ends of the multiple stent structure. For example, gates 266 that connect tube 264 to stent body 232 are severed in FIG. 4C. The gates can be very thin so that they can be easily removed after a spray-coating process. For example, the thickness (or width) of a gate can be between 0.0005" and 0.0035", typically 0.002". In some embodiments, the gates can be perforated about a width segment thereof so as to facilitate breaking off of the gates from the stent bodies of the multiple stent structure. Such perforations can be positioned along any surface of the gate, such as adjacent to the sidewall 312 such that no portion of the gate is left behind after the breaking thereof. In addition, the number of gates can number between one and ten, typically two. Because the weight of the stent is very low (between 1 mg and 50 mg), the number of gates should be minimized to reduce any rough areas caused by severing the connecting and end portion(s) at the at least one gate(s) after a spray-coating process.

In some embodiments, the multiple stent structure can be supported by a mandrel during the coating process. The mandrel may support the structure by engaging the one or more of the severable portion(s). The mandrel may be configured to engage or contact only the severable portion(s) and to make no contact with any of the stent bodies. Additionally, no other portion of the coating device may make contact with the stent bodies which eliminates defects arising from contact points.

In some embodiments, the mandrel may include an elongate member and one or more support portions along its length with a larger diameter than the elongate to provide more rigid support to avoid the deformation to the stent body during the coating process. For example, the diameter of the elongate member may be between 10 and 50% of the support portions. The support portions are adapted to support a multiple stent structure during coating. The elongate member has a diameter less than an inner diameter of a multiple stent structure so that there is no contact between the elongate member and a stent structure mounted on the mandrel. The one or more support portions have an outer diameter the same as the inner diameter of the multiple stent structure. The support portions may have an outer diameter slightly less than the inner diameter of the multiple stent structure, for example, up to 5% less. The support portions may be disks with a width less than or equal to a width of a tube or tab of the end portions or connecting portions. The disk width may be larger than these portions, but not wide enough to contact a stent body.

Figure 7A:
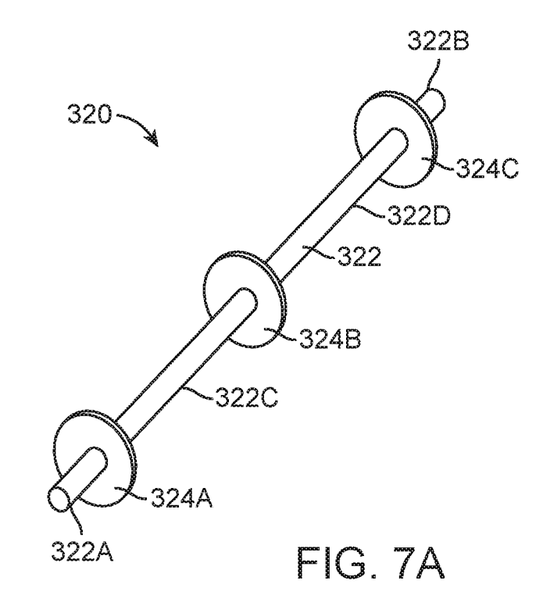
FIG. 7A depicts a mandrel designed to support a multiple stent structure as shown in FIG. 4A.
Figure 8A:
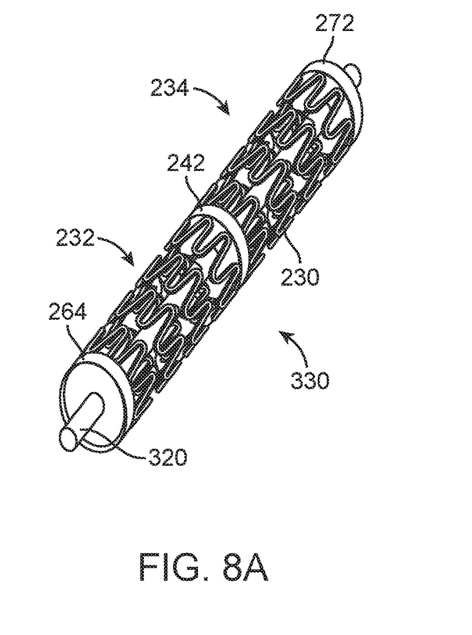
FIG. 8A depicts a multiple stent structure-mandrel assembly.

FIG. 7A depicts a mandrel 320 designed to support a multiple stent structure 230 (see FIG. 4A). Mandrel 320 has an elongate member 322 and three disks 324A, 324B, and 324C disposed along the axis of the elongate member. Elongate member 322 has two end sections 322A and 322B axially proximal and distal from disks 324A and 324C, respectively. Elongate member 322 has a section 322C between disks 324A and 324B and has a section 322D between disks 324B and 324C. As illustrated in FIG. 8A, disks 324A, 324B, and 324C are spaced apart to support multiple stent structure 230 by engaging tubes 264, 242, and 272, respectively.

Figure 7B:
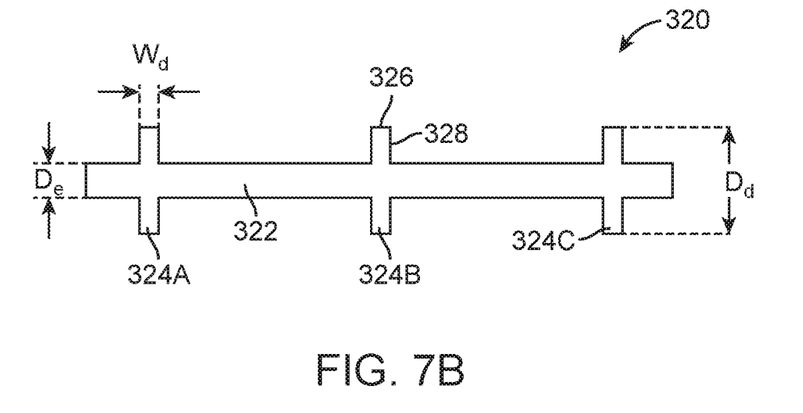
FIG. 7B depicts a longitudinal cross section of the mandrel of FIG. 7A.

FIG. 7B depicts a longitudinal or axial cross section of mandrel 320. Elongate member 322 has a diameter De which is smaller than the diameter Dd of the disks 324A, 324B, and 324C. The disks have outer surfaces 326 and side surfaces 328.

Figure 8B:
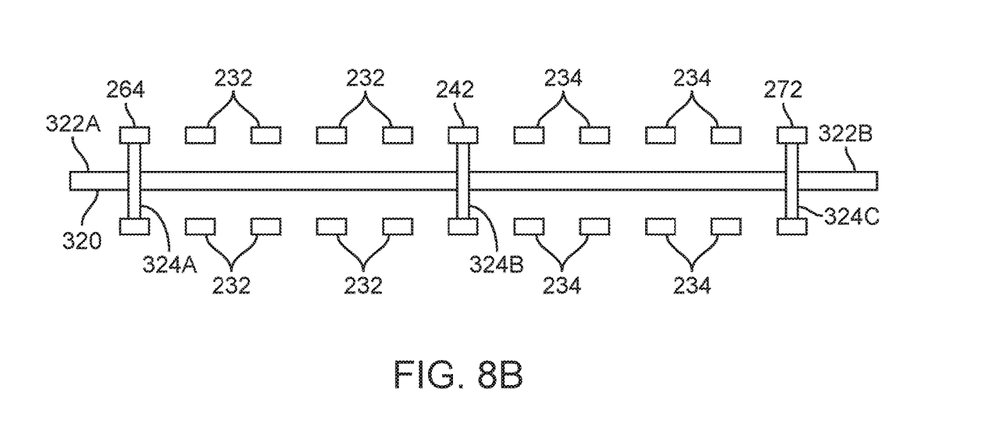
FIG. 8B depicts an axial cross section of assembly of FIG. 8A.

FIG. 8A depicts a multiple stent structure-mandrel assembly 330 including mandrel 320 disposed within multiple stent structure 230. FIG. 8B depicts an axial cross section of assembly 330 with stent 232 and stent 234 shown as strut cross sections. Mandrel 320 may be disposed within structure 230 so the cylindrical axes of the two coincide. Outer surfaces 326 of disks 324A, 324B, and 324C engage or contact the inner surface of tubes 264, 242, and 272, respectively, which provides support to multiple stent structure 230 during a coating operation. End sections 322A and 322B of mandrel 330 may be engaged with support members of a coating device (not shown). The assembly may be rotated, as shown by arrow 356, by a support member during a coating operation 102.

In some embodiments, a mandrel may provide support to some of the tubes of the between the end portions of the multiple stent structure. The mandrel in some embodiments may support the structure only at one or both severable end portions. For example, mandrel 330 may have no disk 324B and supports structure 230 with disks 324A and 324C only. In this and other embodiments, the width of the severable connecting portion (e.g., tube 242) between adjacent stent bodies may be adjusted to provide more stiffness to the multiple stent structure during coating. For example, the tube may be 1 to 3 mm, 3 to 5 mm, 5 to 7 mm, or 7 to 10 mm.

Figure 9:
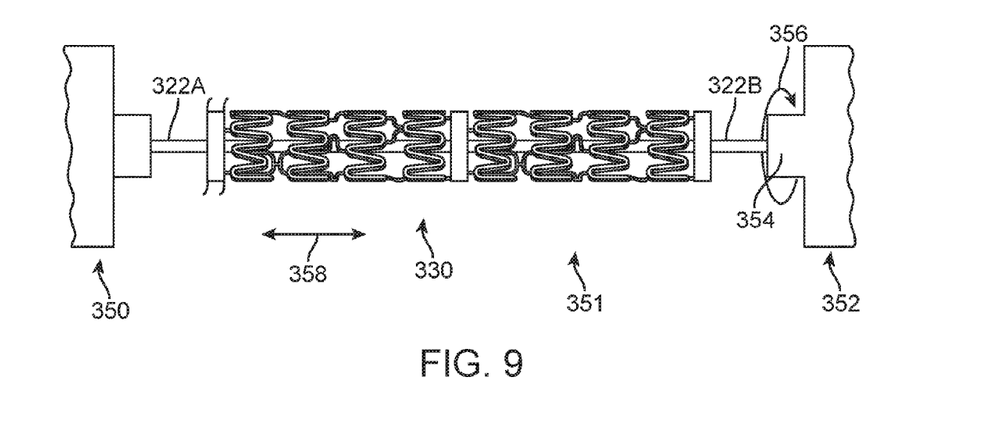
FIG. 9 depicts one embodiment of system for coating a multiple stent structure.

FIG. 9 depicts one embodiment of system 351 for coating a multiple stent structure. The structure-mandrel assembly 330 of FIGS. 8A-B is supported at one end by a support member 350 and another end by support member 352. Section 322A of mandrel 320 is disposed within a recess of support member 350 and section 322B of mandrel 320 is disposed within a recess of support member 352. Support member 352, for example, can include a rotatable spindle 354 that rotates, as shown by arrow 356, structure-mandrel assembly 330 during a coating operation. A nozzle (not shown) can be positioned above assembly 330 which deposits coating material on structure 230. System 351 can be translated linearly as shown by arrow 358 during a coating operation using for example, a system shown in FIG. 8 of U.S. Pat. No. 7,833,261.

Figure 10:
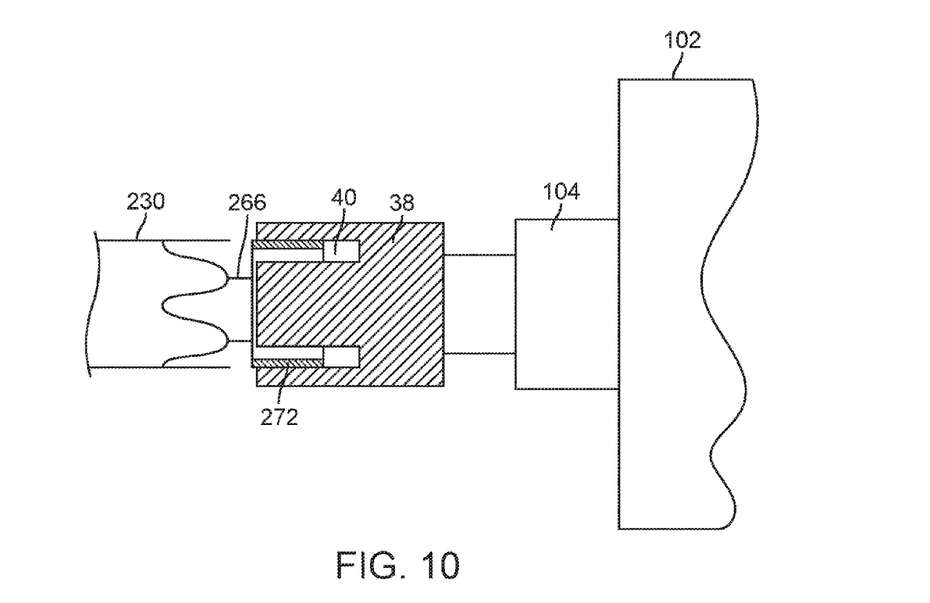
FIG. 10 illustrates one form of a method using the multiple stent structure described in FIG. 4A with a modified version of the spray-coating device of FIG. 2.

In further embodiments, a multiple stent structure can be supported during a coating operation without the use of a mandrel. In such embodiments, the structure can be supported through engagement of one or both end tubes into a tailstock that is coupled to a support member of a coating device. FIG. 10 illustrates one form of a method using the multiple stent structure described in FIG. 4A with a modified version of the spray-coating device 100 of FIG. 2. In some embodiments, end tube 272 can be inserted into a circular opening 40 of a tail stock 38 (see FIG. 10). The tail stock 38 can be cylindrical and between 0.25 inches and 1.0 inch, preferably 0.5 inches in diameter. In addition, the tail stock can be metal, polymer or any combination thereof. The opening 40 can function to secure the end tube 272 when support member 104 is rotating during a spray-coating process. Tail stock 38 can thereafter be mounted onto the support member 104. Alternatively, tail stock 38 can be mounted on support member 104, and end tube 272 can thereafter be inserted into the tail stock 38. In some embodiments, end tube 272 can be press-fitted directly onto support member 104. After positioning, multiple stent structure 230 can then be coated by composition 114 from nozzle 108 (see FIG. 2). In some applications, the stent movement and rotating device 102 can move the multiple stent structure 230 in a linear direction (arrow 116 in FIG. 2) to achieve uniform coating. In some applications, support member 104 can rotate multiple stent structure 230 (arrow 118) to achieve a partial or uniform coating. In some applications, a combination of linear and rotational movements can be used to coat multiple stent structure 230. Other spray-coating techniques known by those skilled in the art can also be used.

After the spray-coating process (or optional drying process), end tube 272 may be detached from the stent structure 230 by mechanically breaking, chemically severing, a combination of mechanical/chemical processing, or laser cutting the at least one gate 274 at the multiple stent structure 230 or at some portion, or junction, along the at least one gate 274. Preferably, detachment is made adjacent to or at the surface of the stent with no portions or minimal portions of the gate left behind. In some embodiments, detachment can be accomplished by holding multiple stent structure 230 and rotating the tube 272 (or vice-versa) with sufficient torque. Additional polishing or touch up techniques at those break points can be implemented to remove any remaining portions of the gate 274 or any roughness caused by the breaking of the at least one gate 274. For example, for polymer stent bodies or scaffolds (such as poly(L-lactide), the break points may be contacted briefly with solvent to smooth out the break points. Examples of solvents which can be used include, but are not limited to, chloroform, acetone, methyl ethyl ketone, or tetrahydrofuran. This smoothing technique is most beneficial if the gate 274 is made from a polymer (e.g., bioabsorbable or biostable polymer disclosed below). Alternatively, a solvent for the polymer can be used to remove or etch away gate 274. The solvent, however, should not adversely affect the coating, the integrity of the multiple stent structure 230 or any therapeutic agent contained on or within multiple stent structure 230.

Advantageously, the multiple stent structures of the present invention eliminate coating defects caused by contact points during coating and allow coating more than one stent body between loading and unloading steps in a coating operation. The structure can be supported by a mandrel by engaging tubes at the ends, 264 and 272 and tubes connecting adjacent stent bodies, e.g., 242, without any contact with stent bodies. The tubes are severable from the stent bodies and are not part of the stent final product to be implanted into a patient.

Also, in some embodiments, the multiple stent structures eliminate the need for a stent holding device, such as a mandrel, in the spray-coating process. That is, end tubes or tabs provide support to the stent when mounted on a spray-coating device, eliminating the need for support that would otherwise be provided by the mandrel. In this manner, coating defects caused by contact between stent bodies of the structure and the mandrel are thereby substantially or completely eliminated.

The multiple stent structures can be made of a metallic material or an alloy such as, but not limited to, stainless steel (316L or 300), "MP35N," "MP2ON," ELASTINITE (Nitinol), Egiloy, tantalum, tantalum alloy, cobalt-chromium alloy, nickel-titanium alloy, platinum, iridium, platinum-iridium alloy, gold, magnesium, or combinations thereof "MP35N" and "MP2ON" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum.

The multiple stent structures may also be made from and/or coated with a biostable polymer or a bioerodable, biodegradable, bioresorbable polymer or any combination thereof. Bioerodable, biodegradable or bioresorbable are intended to be used interchangeably unless otherwise indicated. Also, the stent inner diameter ("ID") can range anywhere between two mm to four mm for coronary stents and five mm to twenty mm for peripheral stents. In some embodiments, a polymeric stent can include other materials, such as layers or deposits of metallic material which can be bioerodable.

Representative examples of polymers which may comprise a polymeric stent and/or a coating thereon are, but are not limited to, fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(L-lactide-co-glycolide); poly(L-lactide-co-glycolide); poly(hydroxybutyrates); poly(hydroxybutyrate-covalerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly (lactic acid); poly(anhydrides), poly(alkylene oxalates); poly(phosphazenes); poly(urethanes); silicones; poly(esters); poly(olefins); copolymers of poly(isobutylene); copolymers of ethylenealphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL); copolymers of acrylonitrilestyrene, ABS resins, and copolymers of ethylene-vinyl acetate; and any derivatives, analogs, homologues, congeners, salts, copolymers and combinations thereof.

In some embodiments, the materials can also include, but are not limited to, poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some embodiments, the polymer can be a poly(ester amide), a poly(lactide) or a poly(lactide-co-glycolide) copolymer; and any derivatives, analogs, homologues, congeners, salts, copolymers and combinations thereof.

In some embodiments, the biodegradable polymers can include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, and any derivatives, analogs, homologues, congeners, salts, copolymers and combinations thereof.

In some embodiments, the biodegradable polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D, L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly (amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In other embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof.

In some embodiments, the polymers are selected such that they specifically exclude any one or any combination of any of the polymers taught herein.

The multiple stent structure described herein may be coated with one or more therapeutic agents, including an anti-proliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazolerapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-argchloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable. In some embodiments, any one of the stent bodies (e.g., 232, 234 in FIG. 4A), gates (e.g., 244, 250 in FIG. 4B), connecting tubes (e.g., 242 in FIG. 4A), end tubes (e.g., 264, 272 in FIG. 4B) or a tab (e.g., 38 in FIG. 5A) can be made of the same material or different materials, such as any of the above-described materials.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. A method of coating a plurality of stents comprising:
    providing a structure comprising a plurality of stent bodies arranged end to end, wherein adjacent stent bodies along the structure are connected by a severable connecting portion disposed between the adjacent stent bodies, the severable connecting portion comprising a tube disposed between the adjacent stent bodies, a first gate connecting the tube to one of the adjacent stent bodies, and a second gate connecting the tube to the other adjacent stent body, wherein the first and second gates are adapted to sever from the adjacent stent bodies or are adapted to break along a segment of the gates;
    depositing a coating on the plurality of stent bodies; and
    severing the first and second gates to disconnect the plurality of stent bodies, wherein the tube is not part of a final stent product to be implanted in a patient.

2. The method of claim 1, wherein at least one of the stent bodies at an end of the structure comprises a severable end portion at the end of the structure.

3. The method of claim 2, further comprising severing the severable end portion from the at least one of the stent bodies after depositing the coating.

4. The method of claim 2, wherein the severable end portion is mounted over a rotatable member that supports and rotates the structure during the depositing of the coating, wherein the rotatable member does not contact any of the stent bodies.

5. The method of claim 2, wherein at both ends of the structure a stent body comprises the severable end portion at the respective end of the structure, and wherein a mandrel disposed within the structure engages the severable end portion at each end of the structure to support the structure during the depositing of the coating.

6. The method of claim 5, wherein at least one end of the mandrel engages a rotatable member that rotates the mandrel and the structure during the depositing of the coating.

\* \* \* \* \*